United States Patent [19]
Goetz et al.

[11] 4,068,077
[45] Jan. 10, 1978

[54] MANUFACTURE OF N-SUBSTITUTED TETRAHYDRO-1,4-OXAZINES

[75] Inventors: Norbert Goetz, Worms; Bernd Zeeh; Martin Decker, both of Ludwigshafen; Leopold Hupfer, Friedelsheim; Herbert Toussaint, Frankenthal, all of Germany

[73] Assignee: BASF Aktiengesellschaft, Ludwigshafen, Germany

[21] Appl. No.: 707,864

[22] Filed: July 22, 1976

[30] Foreign Application Priority Data

Sept. 27, 1975 Germany .............................. 2543279

[51] Int. Cl.$^2$ .................. C07D 265/30; C07D 295/02
[52] U.S. Cl. ..................................... 544/178; 544/174
[58] Field of Search ............................ 260/247, 247.75

[56] References Cited

U.S. PATENT DOCUMENTS 2,597,260   5/1952   Reck ..................................... 260/247

Primary Examiner—Natalie Trousof
Assistant Examiner—R. W. Ramsuer
Attorney, Agent, or Firm—Keil, Thompson & Shurtleff

[57] ABSTRACT

A new process for the manufacture of N-substituted tetrahydro-1,4-oxazines, also called morpholines, by conversion of N-substituted bis-(2-hydroxyalkyl)-amines in the presence of catalysts.

5 Claims, No Drawings

MANUFACTURE OF N-SUBSTITUTED TETRAHYDRO-1,4-OXAZINES

The present invention relates to a new process for the manufacture of N-substituted tetrahydro-1,4-oxazines, also called morpholines, by conversion of N-substituted bis-(2-hydroxyalkyl)-amines in the presence of catalysts. The N-substituted morpholine compounds are valuable intermediates or active ingredients of crop protection agents (German Patents 1,173,722, 1,164,152 and 1,198,125).

The manufacture of morpholines by heating diethanolamines (bis-(2-hydroxyethyl)-amines), or diisopropanolamines (bis-(2-hydroxypropyl)-amines), with excess sulfuric acid and then treating the mixture with alkalis, has been disclosed (Houben-Weyl, "Methoden der organischen Chemie", 6/4, pages 510–546, and U.S. Pat. No. 2,776,972). This process however has the disadvantage that it pollutes the environment, since the neutralization of the sulfuric acid results in a relatively large amount of sulfate (about 2 moles of sulfate are produced per mole of morpholine compound), entailing severely polluted waste waters. The cyclization of bis-(2-hydroxyalkyl)-amines to morpholines by vapor phase dehydration over aluminum oxide and silicate catalysts, at temperatures of from 300° to 400° C, has also been disclosed (U.S. Pat. No. 2,597,260 and German Pat. No. 844,006). A disadvantage of these processes is that large quantities of by-products are formed, which in most cases are difficult to separate from the main product by distillation. Furthermore, the rapid deposition of cracked products on the catalysts leads to rapid loss of their catalytic activity.

We have found that N-substituted morpholines of the general formula I

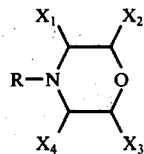

where R is an aliphatic radical of 1 to 20 carbon atoms, a cycloaliphatic radical of 6 to 12 carbon atoms, an araliphatic radical of 7 to 15 carbon atoms or an aryl radical of 6 to 10 carbon atoms and may in addition carry substituents, eg. alkoxy of 1 to 6 carbon atoms, and $X_1$, $X_2$, $X_3$ and $X_4$ are identical or different and each is hydrogen or methyl, are obtained in good yields by cyclizing N-substituted bis-(2-hydroxyalkyl)-amines of the formula II

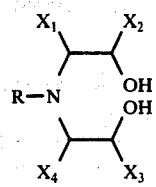

where R, $X_1$, $X_2$, $X_3$ and $X_4$ have the above meaning, if the cyclizing is carried out in the presence of a dehydration catalyst and a hydrogenation is carried out in the presence of hydrogen and a hydrogenation catalyst at from 100° to 300° C, preferably from 180° to 280° C, and at pressures of from atmospheric pressure to 250 atmospheres, especially to 100 atmospheres.

The advantages of the new process are that it does not entail the use of corrosive media, eg. sulfuric acid, and that there is no unavoidable production of alkali metal salts. The catalysts used have a long life, since only small amounts of cracked products are formed. The reaction products are substantially free from impurities. The new process gives very pure compounds which, since they are free from interfering by-products, can also be employed directly as active compounds in crop protection (German Pat. No. 1,214,471). The unsaturated compounds, eg. of the structure

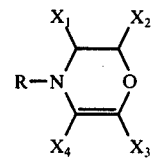

which occur as by-products when cyclizing bis-(2-hydroxyalkyl)-amines, are not formed in the process of the invention.

Examples of the N-substituted bis-(2-hydroxyalkyl)-amines of the formula II which are used as starting compounds for the process are N-methyl-diethanolamine (N-methyl-bis-(2-hydroxyethyl)-amine), N-methyl-diisopropanolamine (N-methyl-bis-(2-hydroxypropyl)-amine), N-ethyl-diethanolamine (N-ethyl-bis-(2-hydroxyethyl)-amine), N-butyl-bis(2-hydroxyethyl)-amine, N-dodecyl-bis-(2-hydroxyethyl)-amine, N-tridecyl-bis-(2-hydroxypropyl)-amine, N-stearyl-bis-(2-hydroxyethyl)-amine, N-cyclohexyl-bis-(2-hydroxyethyl)-amine, N-cyclohexyl-bis-(2-hydroxypropyl)-amine, N-cyclooctyl-bis-(2-hydroxyethyl)-amine, N-cyclooctyl-bis-(2-hydroxypropyl)-amine, N-cyclododecyl-bis-(2-hydroxypropyl)-amine, N-benzyl-bis-(2-hydroxyethyl)-amine and N-phenyl-bis-(2-hydroxyethyl)-amine.

The manufacture of the starting materials is described in Houben-Weyl "Methoden der organischen Chemie", volume 10-1, pages 311 et seq.

The cyclization takes place in accordance with the following equation:

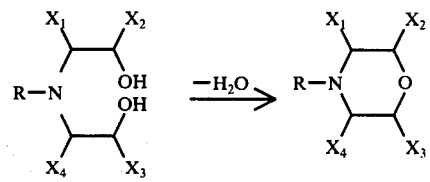

where R, $X_1$, $X_2$, $X_3$ and $X_4$ have the above meanings.

Temperatures of from 100° to 300° C are in general employed for carrying out the cyclization, the range from 180° to 280° C being particularly advantageous. The reaction is usually carried out under normal pressure or under superatmospheric pressure, e.g. up to 250 atmospheres.

The starting materials may be employed in the absence of solvents or after dilution with solvents which are inert under the reaction conditions. Examples of suitable solvents are toluene, xylene, cyclohexane, tetrahydrofuran, mesitylene, diethylbenzene and tetralin.

The cyclization can be carried out in the liquid phase and/or in the gas phase. It may be carried out batchwise, eg. in an autoclave, or continuously, eg. in a fluidized bed reactor or fixed bed reactor. In continuous operation of the process when carried out in a single step, hydrogen or mixtures of hydrogen and nitrogen may be dosed in, to act as a carrier gas.

The cyclizing of the starting materials and the hydrogenation may be carried out in one step or two, depending on the composition of the catalyst used.

Examples of catalyst compositions suitable for the one-step process are those which contain from 0.1 to 40% by weight of one or more heavy metals (cobalt, nickel, copper, chromium, manganese and tungsten) and, if appropriate, from 0.5 to 25% by weight of boric acid and/or from 0.5 to 25% by weight of phosphoric acid, on conventional carriers (aluminum oxide or silica gel), eg. 7.9% by weight of cobalt, 7.9% by weight of nickel and 3.2% by weight of copper on aluminum oxide, 12.6% by weight of cobalt, 0.8% by weight of chromium and 0.95% by weight of phosphoric acid on aluminum oxide, 16% by weight of nickel, 5.5% of copper and 1.3% by weight of manganese on silica gel, 18% by weight of nickel, 6.2% by weight of copper, 1.7% by weight of manganese and 1.3% by weight of phosphoric acid on silica gel, or 20% by weight of aluminum chromate and 0.5% by weight of tungsten on aluminum oxide.

If the two-step method is used, the first step, the cyclizing of the N-substituted bis-(2-hydroxyalkyl)-amines, can be carried out with the conventional catalysts (Houben-Weyl, Methoden der organischen Chemie, volume 6/4, pages 510-546, and German Pat. No. 1,198,125), eg. aluminum oxide, phosphoric acid on silica, phosphoric acid on pumice, aluminum phosphate, boron phosphate, magnesium phosphate, calcium phosphate or cerium phosphate. Suitable catalysts for the hydrogenation in a second step are, in particular, metals of groups Ib, VIa, and VIII of the Periodic Table, eg. copper, silver, chromium, tungsten, cobalt, nickel or palladium (Houben-Weyl, Methoden der organischen Chemie, volume 4/2, pages 283-295).

In general, the reaction products are purified by fractional distillation.

The N-substituted morpholines manufactured by the process of the invention can be used for the manufacture of surface-active agents, anti-corrosion agents or crop protection agents (German Pat. Nos. 1,214,471, 1,164,152 and 1,173,722). Specifically for their use as plant protection agents, it is important that the active compounds produced should be substantially free from by-products and impurities, since these can in certain circumstances be responsible for undersirable side effects, eg. damage to the leaves of crop plants. Using the process according to the invention, the N-substituted morpholines required for crop protection agents are obtained in the requisite purity.

In the Examples parts are by weight, unless stated otherwise, and parts by volume bear the same relation to parts by weight as the liter to the kilogram.

EXAMPLE 1

A vertical tube of 0.80 m length and 50 mm internal diameter is filled with a catalyst which consists of 7.9% of cobalt, 7.9% of nickel and 3.2% of copper on aluminum oxide and is used in the form of 4 mm thick extrudate. The catalyst is first activated stepwise at 180°, 230° and 280° C, whilst introducing 50,000 parts by volume of hydrogen per hour.

The activated catalyst is then heated at 250° C, after which 80 parts of N-tridecyldiisopropanolamine (N-tridecyl-bis-(2-hydroxypropyl)-amine) per hour are introduced at the top of the tube whilst at the same time 100,000 parts by volume of hydrogen per hour are passed over the catalyst as a carrier gas. The aqueous phase is separated off the reaction product obtained, and the organic phase is subjected to fractional distillation. N-Tridecyl-2,6-dimethylmorpholine which is pure according to NMR spectroscopy and boils at 97° C/0.01 mm Hg is obtained. The yield is 85% of theory, based on N-tridecyldiisopropanolamine employed.

EXAMPLE 2

The apparatus described in Example 1 is filled with a catalyst which consists of 20% of aluminum chromate and 0.5% of tungsten on aluminum oxide.

The catalyst is heated at 240° C. 40 parts of tridecyldiisopropanolamine per hour and 10,000 parts by volume of hydrogen per hour are then passed over the heated catalyst. The reaction product is worked up as described in Example 1. N-Tridecyl-2,6-dimethylmorpholine which is pure according to NMR spectroscopy is obtained in a yield of 87% of theory (based on N-tridecyldiisopropanolamine employed).

EXAMPLE 3

Using the apparatus described in Example 1, 30 parts of N-cyclododecyldiisopropanolamine per hour are passed over the catalyst described in more detail in Example 1. The catalyst is heated at 260° C and 10,000 parts by volume of hydrogen per hour are introduced as a carrier gas. On working up the reaction product by distillation, N-cyclododecyl-2,6-dimethylmorpholine which is pure according to NMR spectroscopy and boils at 109° C/0.01 mm Hg is obtained. The yield is 78% of theory, based on N-cyclododecyldiisopropanolamine employed.

EXAMPLE 4

The apparatus described in Example 1 is filled with a boron phosphate catalyst, which is heated at 210° C. 30 parts of N-tridecyldiisopropanolamine and 10,000 parts by volume of nitrogen per hour are then passed simultaneously over the heated catalyst.

500 parts of the reaction product and 20 parts of Raney nickel are introduced into a 1 l stirred autoclave, which is heated at 150° C, and after reaching this temperature hydrogen is injected until the total pressure reaches 100 atmospheres. The autoclave is kept for 15 hours under these reaction conditions, which are maintained constant.

The reaction product is then filtered and the filtrate is subjected to fractional distillation. This gives N-tridecyl-2,6-dimethylmorpholine which is pure according to NMR spectroscopy. The yield is 85% of theory, based on N-tridecyldiisopropanolamine employed.

EXAMPLE 5

The apparatus described in more detail in Example is filled with a catalyst which consists of 20% of phosphoric acid on silica gel and the catalyst is heated at 230° C. 40 parts of N-tridecyldiisopropanolamine and 5,000 parts by volume of nitrogen per hour are then passed simultaneously over the heated catalyst.

100 parts of the reaction product thus obtained, mixed with 6 parts of Raney nickel, are hydrogenated for 5 hours in a 250 ml shaken autoclave at 180° C under a constant hydrogen pressure of 100 atmospheres. The reaction product is filtered and the filtrate is worked up by distillation. Here again, N-tridecyl-2,6-dimethylmorpholine which is pure according to NMR spectroscopy is obtained. The yield is 83% of theory, based on N-tridecyldiisopropanolamine employed.

EXAMPLE 6

A 250 ml shaken autoclave is charged with 50 parts of N-methyldiisopropanolamine, 50 parts of toluene and 10 parts of a catalyst which consists of 7.9% of cobalt, 7.9% of nickel and 3.2% of copper on aluminum oxide and has been activated in a stream of hydrogen in accordance with the instructions given in Example 1. The autoclave is heated for 10 hours at 210° C under a constant hydrogen pressure of 60 atmospheres.

The catalyst is then separated from the reaction product by filtration. On working up the filtrate by distillation, N-methyl-2,6-dimethylmorpholine which is pure according to NMR spectroscopy and boils at 72° C/70 mm Hg is obtained. The yield is 73% of theory, based on N-methyldiisopropanolamine employed.

EXAMPLE 7

A 250 ml shaken autoclave is charged with 50 parts of N,N-bis-(2-hydroxyethyl)-aniline, 50 parts of toluene and 10 parts of a catalyst which consists of 7.9% of cobalt, 7.9% of nickel and 3.2% of copper on aluminum oxide and has been activated in a stream of hydrogen in accordance with the instructions given in Example 1.

The autoclave is heated for 10 hours at 240° C under a constant hydrogen pressure of 70 atmospheres. The resulting reaction product is filtered and the catalyst which has been filtered off is washed with toluene. The filtrate is freed from the solvent under reduced pressure and the residue is distilled under reduced pressure. Pure N-phenylmorpholine melting at 53°-54° C is obtained. The yield is 83% of theory, based on N,N-bis-(2-hydroxyethyl)-aniline employed.

EXAMPLE 8

The procedure followed is as described in Example 7, but N,N-bis-(2-hydroxyethyl)-cyclohexylamine is used as the starting material. On working up the reaction product by distillation, N-cyclohexylmorpholine, boiling at 240° C/760 mm Hg is obtained. The yield is 81% of theory, based on N,N-bis-(2-hydroxyethyl)-cyclohexylamine employed.

EXAMPLE 9

The apparatus described in Example 1 is filled with a catalyst which consists of 7.9% of cobalt, 7.9% of nickel and 3.2% of copper on aluminum oxide and has been impregnated with 10% of boron phosphate. The catalyst is activated in accordance with the instructions given in Example 1 and is then heated at 240° C. 80 parts of N-tridecyldiisopropanolamine per hour are then passed over the heated catalyst. On working up the reaction product by distillation, N-tridecyl-2,6-dimethylmorpholine which is pure according to NMR spectroscopy is obtained. The yield is 94% of theory (based on N-tridecyldiisopropanolamine employed).

We claim:

1. A process for the manufacture of an N-substituted morpholine substantially free from impurities of the general formula I

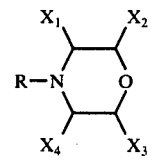

where R is an aliphatic radical of 1 to 20 carbon atoms, a cycloaliphatic radical of 6 to 12 carbon atoms, an araliphatic radical of 7 to 15 carbon atoms or an aryl radical of 6 to 10 carbon atoms, and $X_1$, $X_2$, $X_3$ and $X_4$ are identical or different and each is hydrogen or methyl, by cyclizing a compound of the general formula II

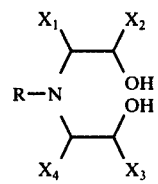

where R, $X_1$, $X_2$, $X_3$ and $X_4$ have the above meaning, wherein the cyclizing is carried out in the presence of a dehydration catalyst and a hydrogenation is carried out in the presence of hydrogen and a hydrogenation catalyst respectively at from 100° to 300° C and at pressures of from atmospheric pressure to 250 atmospheres.

2. A process as claimed in claim 1, wherein the dehydration catalyst is aluminum oxide, phosphoric acid or a phosphate of boron, aluminum, magnesium, calcium or cerium.

3. A process as claimed in claim 1 wherein the cyclizing and the hydrogenation are carried out together by using a catalyst containing both a catalytically active dehydrogeniion compound and a catalytically active hydrogenation metal.

4. A process as claimed in claim 3 wherein said catalyst contains 0.1 to 40% by weight of one or more of the metals cobalt, nickel, copper, chromium, manganese and tungsten as the catalytically active hydrogenation metal.

5. A process as claimed in claim 1 wherein said hydrogenation catalyst comprises metals selected from the group consisting of copper, silver, chromium, tungsten, cobalt, nickel or palladium.

* * * * *